United States Patent [19]
Bratz et al.

[11] Patent Number: 6,133,202
[45] Date of Patent: Oct. 17, 2000

[54] CYCLOHEXENONE OXIME ETHER METAL SALTS

[75] Inventors: Matthias Bratz; Karl-Friedrich Jäger, both of Limburgerhof; Remy Benoit, Neustadt; Harald Rang, Altrip; Ulf Misslitz, Neustadt; Karl-Otto Westphalen, Speyer, all of Germany

[73] Assignee: BASF Aktiengesellschaft, Ludwigshafen, Germany

[21] Appl. No.: 09/077,925

[22] PCT Filed: Nov. 28, 1996

[86] PCT No.: PCT/EP96/05255

§ 371 Date: Jun. 5, 1998

§ 102(e) Date: Jun. 5, 1998

[87] PCT Pub. No.: WO97/20807

PCT Pub. Date: Jun. 12, 1997

[30] Foreign Application Priority Data

Dec. 5, 1995 [DE] Germany ............... 195 45 212

[51] Int. Cl.$^7$ ............... A01N 43/40; C07D 405/00
[52] U.S. Cl. ............... 504/244; 504/251; 504/254; 504/260; 504/289; 504/294; 504/295; 546/200; 546/283; 546/284; 548/247; 548/517
[58] Field of Search ............... 504/244, 251, 504/254, 260, 289, 294, 295; 546/200, 283, 284; 548/247, 517

[56] References Cited

U.S. PATENT DOCUMENTS

| | | | |
|---|---|---|---|
| 4,741,768 | 5/1988 | Frazier et al. | 71/98 |
| 4,952,722 | 8/1990 | Serban et al. | 560/250 |
| 5,022,914 | 6/1991 | Kast et al. | 71/88 |
| 5,110,989 | 5/1992 | Serban et al. | 568/327 |
| 5,190,573 | 3/1993 | Misslitz et al. | 504/292 |
| 5,228,896 | 7/1993 | Misslitz et al. | 504/288 |
| 5,250,505 | 10/1993 | Kast et al. | 504/292 |
| 5,330,965 | 7/1994 | Misslitz et al. | 504/244 |
| 5,364,833 | 11/1994 | Kast et al. | 504/289 |
| 5,374,609 | 12/1994 | Kast et al. | 504/344 |
| 5,411,936 | 5/1995 | Kast et al. | 504/244 |
| 5,563,114 | 10/1996 | Meyer et al. | 504/288 |
| 5,574,000 | 11/1996 | Kast et al. | 504/292 |

FOREIGN PATENT DOCUMENTS

| | | |
|---|---|---|
| 085530 | 8/1983 | European Pat. Off. . |
| 266068 | 5/1988 | European Pat. Off. . |
| 39 41 160 | 12/1989 | Germany . |
| 78-034753 | 7/1980 | Japan . |
| 59-163363 | 3/1983 | Japan . |
| 62-089653 | 9/1985 | Japan . |

OTHER PUBLICATIONS

*The Pesticide Manual*, 9th Ed., 1991, pp. 21–22.

*Primary Examiner*—Porfirio Nazario-Gonzalez
*Attorney, Agent, or Firm*—Keil & Weinkauf

[57] ABSTRACT

Herbicidally active cyclohexenone oxime ether metal salts of formula I

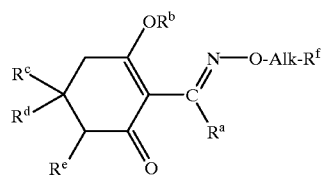

where $R^a$, $R^b$, $R^c$, $R^d$, $R^e$, Alk and $R^f$ are as defined in the specification disclosure, having an improved shelf life and thermal stability and reduced water vapor uptake.

9 Claims, 2 Drawing Sheets

CYCLOHEXENONE OXIME ETHER METAL SALTS

The present invention relates to novel cyclohexenone oxime ether metal salts of the formula I

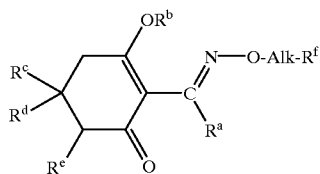

where the variables have the following meanings:

$R^a$ is $C_1$–$C_6$-alkyl;

$R^b$ is the equivalent of an alkali metal, alkaline earth metal or transition metal;

$R^c$ is hydrogen, cyano, formyl, $C_1$–$C_6$-alkyl, $C_1$–$C_4$-alkoxy-$C_1$–$C_6$-alkyl, $C_1$–$C_4$-alkylthio-$C_1$–$C_6$-alkyl, a phenoxy-$C_1$–$C_6$-alkyl, phenylthio-$C_1$–$C_6$-alkyl, pyridyloxy-$C_1$–$C_6$-alkyl or pyridylthio-$C_1$–$C_6$-alkyl group, it being possible for the phenyl and pyridyl rings of these groups to have attached to them, if desired, one to three substituents, in each case selected from the group consisting of nitro, cyano, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_3$–$C_6$-alkenyl, $C_3$–$C_6$-alkenyloxy, $C_3$–$C_6$-alkynyl, $C_3$–$C_6$-alkynyloxy and —$NR^gR^h$, where $R^g$ is hydrogen, $C_1$–$C_4$-alkyl, $C_3$–$C_6$-alkenyl, $C_3$–$C_6$-alkynyl, $C_1$–$C_6$-acyl or benzoyl which, if desired, can have attached to it, in turn, a further one to three radicals, in each case selected from the group consisting of nitro, cyano, halogen, $C_1$–$C_4$-alkyl, $C_1$–$C_4$-haloalkyl, $C_1$–$C_4$-alkoxy and $C_1$–$C_4$-alkythio and $R^h$ is hydrogen, $C_1$–$C_4$-alkyl, $C_3$–$C_6$-alkenyl or $C_3$–$C_6$-alkynyl;

a $C_3$–$C_7$-cycloalkyl group or a $C_5$–$C_7$-cycloalkenyl group, it being possible for these groups, if desired, to have attached to them one to three substituents, in each case selected from the group consisting of hydroxyl, halogen, $C_1$–$C_4$-alkyl, $C_1$–$C_4$-haloalkyl, $C_1$–$C_4$-alkoxy, $C_1$–$C_4$-alkylthio, benzylthio, $C_1$–$C_4$-alkylsulfonyl and $C_1$–$C_4$-alkylsulfinyl;

a 5-membered saturated heterocycle which, in addition to carbon atoms, contains one or two oxygen or sulfur atoms or one oxygen and one sulfur atom as ring members and which, if desired, can additionally have attached to it one to three substituents, in each case selected from the group consisting of $C_1$–$C_4$-alkyl, $C_1$–$C_4$-haloalkyl, $C_1$–$C_4$-alkoxy and $C_1$–$C_4$-alkylthio;

a 6- or 7-membered saturated or mono- or diunsaturated heterocycle which, in addition to carbon atoms, additionally contains one or two oxygen or sulfur atoms or one oxygen and one sulfur atom as ring members and which, if desired, can additionally have attached to it one to three substituents, in each case selected from the group consisting of hydroxyl, halogen, $C_1$–$C_4$-alkyl, $C_1$–$C_4$-haloalkyl, $C_1$–$C_4$-alkoxy and $C_1$–$C_4$-alkylthio;

a 5-membered heteroaromatic ring which, in addition to carbon atoms, contains one or two nitrogen atoms and one oxygen or sulfur atom, or one to three nitrogen atoms, or one oxygen or one sulfur atom as ring members and which, if desired, can additionally have attached to it one to three substituents, in each case selected from the group consisting of cyano, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_2$–$C_6$-alkenyl, $C_2$–$C_6$-alkenyloxy, $C_3$–$C_6$-alkynyloxy and $C_1$–$C_4$-alkoxy-$C_1$–$C_4$-alkyl;

phenyl- or pyridyl, both of which can, if desired, have attached to them one to three substituents, in each case selected from the group consisting of nitro, cyano, formyl, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_3$–$C_6$-alkenyl, $C_3$–$C_6$-alkenyloxy, $C_3$–$C_6$-alkynyl, $C_3$–$C_6$-alkynyloxy and —$NR^kR^l$, where $R^k$ is hydrogen, $C_1$–$C_4$-alkyl, $C_3$–$C_6$-alkenyl or $C_3$–$C_6$-alkynyl and $R^l$ is hydrogen, $C_1$–$C_4$-alkyl, $C_3$–$C_6$-alkenyl, $C_3$–$C_6$-alkynyl, $C_1$–$C_6$-acyl or benzoyl which, if desired, can additionally have attached to it, in turn, one to three substituents, in each case selected from the group consisting of nitro, cyano, halogen, $C_1$–$C_4$-alkyl, $C_1$–$C_4$-haloalkyl, $C_1$–$C_4$-alkoxy and $C_1$–$C_4$-alkylthio;

$R^d$ is hydrogen, hydroxyl or, if $R^c$ is $C_1$–$C_6$-Alkyl, also $C_1$–$C_6$-alkyl;

$R^e$ is hydrogen, cyano, halogen, ($C_1$–$C_4$-alkoxy)carbonyl or ($C_1$–$C_4$-alkyl)ketoxime;

Alk is a $C_1$–$C_6$-alkylene chain, $C_3$–$C_6$-alkenylene chain or $C_3$–$C_6$-alkynylene chain, each of which can have attached to it a methylene group (=$CH_2$) and/or one to three substituents, in each case selected from the group consisting of halogen and $C_1$–$C_3$-alkyl;

a 3- to 6-membered alkylene or 4- to 6-membered alkenylene chain which, if desired, can have attached to it one to three $C_1$–$C_3$-alkyl substituents and which, in addition to methylene or methine units, contains one of the following bridge members: oxygen, sulfur, —SO—, —$SO_2$— or —$N(R^i)$—, where $R^i$ is hydrogen, $C_1$–$C_4$-alkyl, $C_3$–$C_6$-alkenyl or $C_3$–$C_6$-alkynyl;

$R^f$ is the phenyl group, a halophenyl or a dihalophenyl group, it being possible for each phenyl ring, if desired, to have attached to it one to three substituents, in each case selected from the group consisting of nitro, cyano, formyl, halogen, $C_1$–$C_4$-alkyl, $C_1$–$C_4$-haloalkyl, $C_1$–$C_4$-alkoxy, $C_1$–$C_4$-haloalkoxy, $C_3$–$C_6$-alkenyl, $C_3$–$C_6$-alkenyloxy, $C_3$–$C_6$-alkynyl, $C_3$–$C_6$-alkynyloxy and —$NR^kR^l$, where $R^k$ is hydrogen, $C_1$–$C_4$-alkyl, $C_3$–$C_6$-alkenyl or $C_3$–$C_6$-alkynyl and $R^l$ is hydrogen, $C_1$–$C_4$-alkyl, $C_3$–$C_6$-alkenyl, $C_3$–$C_6$-alkynyl, $C_1$–$C_6$-acyl or benzoyl which, if desired, can additionally have attached to it, in turn, one to three radicals, in each case selected from the group consisting of nitro, cyano, halogen, $C_1$–$C_4$-alkyl, $C_1$–$C_4$-haloalkyl, $C_1$–$C_4$-alkoxy and $C_1$–$C_4$-alkylthio.

The invention furthermore relates to the use of the compounds I as herbicides, herbicidal compositions which comprise the compounds I as active ingredients, processes for the preparation of the compounds I and of herbicidal compositions using the compounds I, and methods of controlling undesirable vegetation using the compounds I.

With crop protection products, it is generally desirable to improve the specific (here: herbicidal) activity and the reliability of their action. The chemical stability of the active ingredient and the shelf life of the finished crop protection formulation are essential. In addition, a certain stability of the active ingredient itself in the environment for a brief period after application is also desirable.

EP-A 266 068 discloses that herbicides from the class of the cyclohexenone oxime ethers tend to decompose. Storage of their ready-to-use preparations over a prolonged period at elevated temperatures is especially critical.

Also decisive besides this long-term stability is the short-term resistance to thermal stress of a compound during its preparation and formulation as a crop protection product, for example during purification or drying operations.

In the class of the cyclohexenone oxime ethers, not only the free compounds, but also their salts, are usually disclosed as being herbicidally active (see, for example, JP-A 59/163363: sodium salts, potassium salts, calcium salts, magnesium salts, barium salts, nickel salts, manganese salts, cobalt salts, zinc salts and iron salts).

JP-A 78/034753 relates to the preparation of sodium salts, potassium salts, calcium salts, magnesium salts, barium salts, nickel salts, copper salts, manganese salts, cobalt salts, zinc salts, iron salts and silver salts of specific 2-alkyloxy-, 2-alkenyloxy-, 2-alkynyloxy- and 2-benzyloxyiminoalkyl-cyclohexenones.

JP-A 62/089653 discloses the lithium salts of specific cyclohexanedione derivatives which are said to form stable crystals.

U.S. Pat. No. 4,741,768 discloses the copper, lithium and magnesium salts of certain 2-[1-(3-chloroallyloxyimino) alkylidene]cyclohexane-1,3-diones which have improved storage stability with respect to temperature and (atmospheric) humidity. However, one specific lithium salt is considered as being highly hygroscopic.

EP-A 085 530 and U.S. Pat. No. 4,952,722 list, besides a large number of cyclohexenone oxime ethers, some salts, the cation in the EP publication being lithium, sodium, potassium or 1/2 copper and in the U.S. publication lithium, sodium, 1/2 copper or 1/2 nickel. However, the salts are not described as having any specific advantage.

DE-A 39 41 160 disclose s storage-stable salts of acyl-cyclohexanedione oxime ethers which act as herbicides and plant growth regulators and which are also said to have an improved stability in the soil compared with the free compounds. Salts having a lithium, sodium, potassium, 1/2 magnesium, 1/2 calcium, 1/2 barium, 1/2 copper(II) or 1/2 zinc cation are mentioned explicitly. However, the fact that the salts frequently crystallize together with solvent during their preparation is also mentioned. However, this would be disadvantageous for later use in crop protection products.

Finally, the active ingredient 2-(1-allyloxyiminobutyl)-4-methoxycarbonyl-5,5-dimethyl-3-oxo-cyclohexenol (common name: ALLOXYDIM) is commercially available in the form of the sodium salt (cf. Meded.FAc.Landbouw-wet. 1977, 42(2,Pt.2), 1597–1614; The Pesticide Manual, 9th Ed. 1991, p. 21).

Thus, since the salts of cyclohexenone oxime ethers having a variety of cations have previously been described, a deduction as to which salts of the free compounds (II; $R^b$ would thus be H) on which I are based have particularly good properties with respect to shelf life, thermal stability, susceptibility to moisture or biological action, is not possible.

It was therefore an object of the present invention to provide herbicidal active ingredients having better physical properties, starting from the cyclohexenone oxime ethers (II).

We have found that this object is achieved by the present cyclohexenone oxime ether metal salts of the formula I. We have furthermore found herbicidal compositions which comprise the compounds I and which are potent herbicides. We have furthermore found that the salts I have outstanding shelf lives. Moreover, these salts are not hygroscopic and more resistant to thermal stress than the free acids (II), which is confirmed by DSC undertakings which show that thermal decomposition only starts above 100° C.

We have furthermore found processes for the preparation of the compounds I, and of compositions comprising them, and methods of controlling undesirable vegetation using the compounds I.

Figure 1:
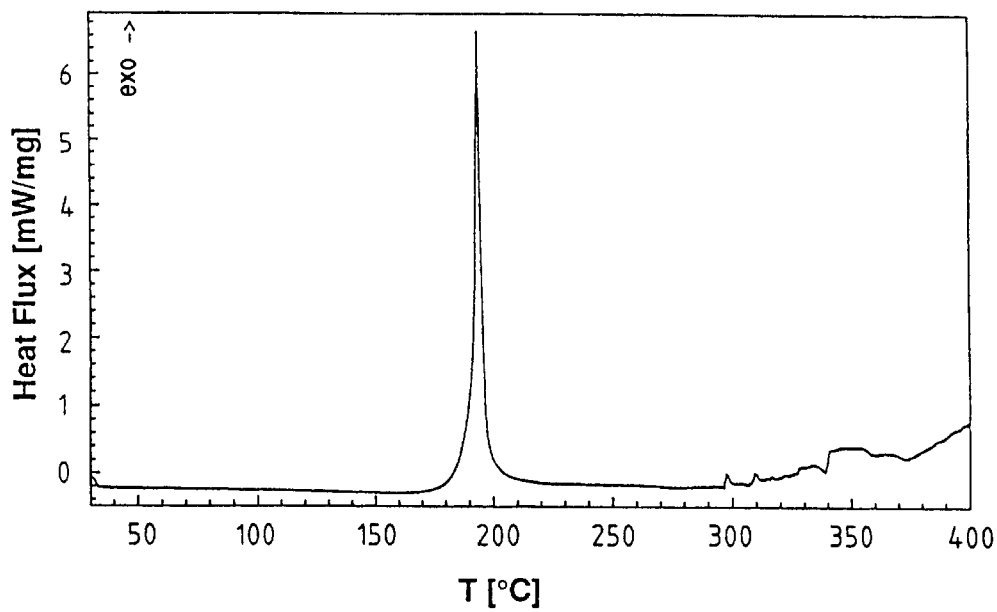
FIG. 1: DSC plot of the lithium salt of 2-{1-[2-(4-chlorophenoxy)propyloximino]butyl}-5-tetrahydrothiopyran-3-ylcyclohexane-1,3-dione.

The free cyclohexenone oxime ethers of the formula II on which the salts I are based

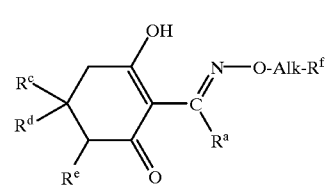

where $R^a$, $R^c$ to $R^f$ and Alk have the same meanings as in formula I are disclosed for example in EP-A 368 227, DE-A 40 14 983, DE-A 40 14 984, DE-A 40 14 986, DE-A 40 14 988 and in U.S. Pat. No. 5,228,896.

Suitable active ingredients are not only the pure enantiomers I, but also their racemates or diastereomer mixtures.

The organic moieties mentioned for $R^a$ and $R^c$ to $R^f$ and for the substituents on "Alk" or on (hetero)cycles are collective terms for individual enumerations of the individual group members. All hydrocarbon chains, ie. all alkyl, haloalkyl, alkylsulfonyl, alkylsulfinyl, alkoxy, haloalkoxy, alkylthio, alkenyl, alkenyloxy, alkynyl, alkynyloxy and acyl moieties can be straight-chain or branched. Halogenated substituents preferably have attached to them one to five identical or different halogen atoms. The meaning halogen is in each case fluorine, bromine, chlorine or iodine, in particular fluorine or chlorine.

Especially preferred cyclohexenone oxime ether metal salts of the formula I are those where the substituents have the following meanings, in each case alone or in combination:

$R^a$ is ethyl- or n-propyl;

$R^b$ is an alkali metal ion or the equivalent of an alkaline earth metal cation, in particular a lithium ion, sodium ion, potassium ion or the equivalent of a magnesium ion; lithium is very particularly preferred;

$R^c$ is a 6- or 7-membered saturated or mono- or diunsaturated heterocycle which, in addition to carbon atoms, contains one or two oxygen or sulfur atoms or one oxygen and one sulfur atom as ring members and which, if desired, can additionally have attached to it one to three substituents, in each case selected from the group consisting of hydroxyl, halogen, $C_1$–$C_4$-alkyl, $C_1$–$C_4$-haloalkyl, $C_1$–$C_4$-alkoxy and $C_1$–$C_4$-alkylthio, in particular tetrahydropyran-3-yl, tetrahydropyran-4-yl and tetrahydrothiopyran-3-yl;

$R^d$ and $R^e$ are in each case hydrogen;

Alk is a 3- to 6-membered alkylene chain which, if desired, can have attached to it a $C_1$–$C_3$-alkyl substituent and which, in addition to methylene or methine units, contains one oxygen or sulfur atom as bridge member, in particular ethyleneoxy or 1,2-propyleneoxy;

Rf is halophenyl, in particular 4-fluorophenyl or 4-chlorophenyl.

The cyclohexenone oxime ether metal salts Ia (=I where $R^b$=Li; $R^d$, $R^e$=H), in particular the compounds listed in Table 1, have proved particularly suitable:

ing compounds Ia.01–Ia.032 only by the fact that $R^b$ is the equivalent of a magnesium ion:

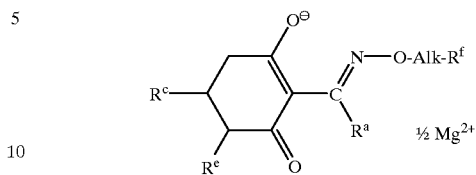

Ib

According to existing findings, the compounds No. Ia.18 and Ib.18 have proved to be very especially advantageous.

In general, the cyclohexenone oxime ether metal salts I are accessible by reacting the corresponding free compound (II) with a hydride, hydroxide, alcoholate or carbonate of the desired metal ion.

It is especially advantageous to start from a solution of (II), as it is obtained when the latter is prepared from III and IV (see, for example, EP-A 456 112), ie. without previous isolation of II:

TABLE 1

Ia

| No. | $R^a$ | $R^c$ | Alk | $R^f$ |
|---|---|---|---|---|
| Ia.01 | $C_2H_5$ | tetrahydrothiopyran-3-yl | —(CH$_2$)$_2$—O— | 4-Cl-phenyl |
| Ia.02 | n-$C_3H_7$ | tetrahydrothiopyran-3-yl | —(CH$_2$)$_2$—O— | 4-Cl-phenyl |
| Ia.03 | $C_2H_5$ | tetrahydropyran-3-yl | —(CH$_2$)$_2$—O— | 4-Cl-phenyl |
| Ia.04 | n-$C_3H_7$ | tetrahydropyran-3-yl | —(CH$_2$)$_2$—O— | 4-Cl-phenyl |
| Ia.05 | $C_2H_5$ | tetrahydrothiopyran-3-yl | —(CH$_2$)$_2$—O— | 4-F-phenyl |
| Ia.06 | n-$C_3H_7$ | tetrahydrothiopyran-3-yl | —(CH$_2$)$_2$—O— | 4-F-phenyl |
| Ia.07 | $C_2H_5$ | tetrahydropyran-3-yl | —(CH$_2$)$_2$—O— | 4-F-phenyl |
| Ia.08 | n-$C_3H_7$ | tetrahydropyran-3-yl | —(CH$_2$)$_2$—O— | 4-F-phenyl |
| Ia.09 | $C_2H_5$ | tetrahydrothiopyran-4-yl | —(CH$_2$)$_2$—O— | 4-Cl-phenyl |
| Ia.10 | n-$C_3H_7$ | tetrahydrothiopyran-4-yl | —(CH$_2$)$_2$—O— | 4-Cl-phenyl |
| Ia.11 | $C_2H_5$ | tetrahydropyran-4-yl | —(CH$_2$)$_2$—O— | 4-Cl-phenyl |
| Ia.12 | n-$C_3H_7$ | tetrahydropyran-4-yl | —(CH$_2$)$_2$—O— | 4-Cl-phenyl |
| Ia.13 | $C_2H_5$ | tetrahydrothiopyran-4-yl | —(CH$_2$)$_2$—O— | 4-F-phenyl |
| Ia.14 | n-$C_3H_7$ | tetrahydrothiopyran-4-yl | —(CH$_2$)$_2$—O— | 4-F-phenyl |
| Ia.15 | $C_2H_5$ | tetrahydropyran-4-yl | —(CH$_2$)$_2$—O— | 4-F-phenyl |
| Ia.16 | n-$C_3H_7$ | tetrahydropyran-4-yl | —(CH$_2$)$_2$—O— | 4-F-phenyl |
| Ia.17 | $C_2H_5$ | tetrahydrothiopyran-3-yl | —CH$_2$CH(CH$_3$)—O— | 4-Cl-phenyl |
| Ia.18 | n-$C_3H_7$ | tetrahydrothiopyran-3-yl | —CH$_2$CH(CH$_3$)—O— | 4-Cl-phenyl |
| Ia.19 | $C_2H_5$ | tetrahydropyran-3-yl | —CH$_2$CH(CH$_3$)—O— | 4-Cl-phenyl |
| Ia.20 | n-$C_3H_7$ | tetrahydropyran-3-yl | —CH$_2$CH(CH$_3$)—O— | 4-Cl-phenyl |
| Ia.21 | $C_2H_5$ | tetrahydrothiopyran-3-yl | —CH$_2$CH(CH$_3$)—O— | 4-F-phenyl |
| Ia.22 | n-$C_3H_7$ | tetrahydrothiopyran-3-yl | —CH$_2$CH(CH$_3$)—O— | 4-F-phenyl |
| Ia.23 | $C_2H_5$ | tetrahydropyran-3-yl | —CH$_2$CH(CH$_3$)—O— | 4-F-phenyl |
| Ia.24 | n-$C_3H_7$ | tetrahydropyran-3-yl | —CH$_2$CH(CH$_3$)—O— | 4-F-phenyl |
| Ia.25 | $C_2H_5$ | tetrahydrothiopyran-4-yl | —CH$_2$CH(CH$_3$)—O— | 4-Cl-phenyl |
| Ia.26 | n-$C_3H_7$ | tetrahydrothiopyran-4-yl | —CH$_2$CH(CH$_3$)—O— | 4-Cl-phenyl |
| Ia.27 | $C_2H_5$ | tetrahydropyran-4-yl | —CH$_2$CH(CH$_3$)—O— | 4-Cl-phenyl |
| Ia.28 | n-$C_3H_7$ | tetrahydropyran-4-yl | —CH$_2$CH(CH$_3$)—O— | 4-Cl-phenyl |
| Ia.29 | $C_2H_5$ | tetrahydrothiopyran-4-yl | —CH$_2$CH(CH$_3$)—O— | 4-F-phenyl |
| Ia.30 | n-$C_3H_7$ | tetrahydrothiopyran-4-yl | —CH$_2$CH(CH$_3$)—O— | 4-F-phenyl |
| Ia.31 | $C_2H_5$ | tetrahydropyran-4-yl | —CH$_2$CH(CH$_3$)—O— | 4-F-phenyl |
| Ia.32 | n-$C_3H_7$ | tetrahydropyran-4-yl | —CH$_2$CH(CH$_3$)—O— | 4-F-phenyl |

Other especially preferred cyclohexenone oxime ether metal salts are those of the formula Ib, in particular the compounds Ib.01 to Ib.32, which differ from the correspond-

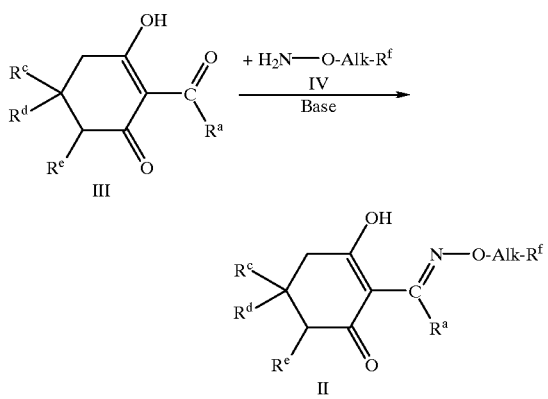

Suitable solvents for II are, in particular, water or solvents which are miscible with water, eg. ethers, such as tetrahydrofuran and dioxane, or lower alcohols, such as methanol and ethanol.

The metal hydride, hydroxide, alkoxide or carbonate is generally employed in solid form or dissolved or suspended in one of the abovementioned solvents.

II is normally neutralized at from $(-100)°$ C. to $200°$ C., preferably from $(-40)°$ C. to $120°$ C., in particular from $(-10)°$ C. to $80°$ C.

The water of reaction formed is preferably removed by means of azeotropic distillation. After the lower-boiling components have been removed, the dry cyclohexenone oxime ether metal salt I is obtained in crystalline or amorphous form.

A process variant consists in dissolving the free compound II in an inert solvent which is not miscible with water, eg. an ether such as diethyl ether, diisopropyl ether, methyl tert-butyl ether, a ketone such as acetone, an aromatic such as toluene and the xylenes, a halohydrocarbon such as methylene chloride, chloroform and 1,2-dichloroethane, or a higher alcohol such as 2-ethylhexanol, and to neutralize the solution with a metal hydride, hydroxide, alkoxide or carbonate, solid or dissolved or suspended in water or in a lower alcohol.

The cyclohexenone oxime ether metal salt I which has formed either precipitates from the reaction mixture as a solid or is obtained in amorphous or crystalline form after removing the solvent.

A further variant consists in reacting II with an approximately equimolar amount of an alcoholate of the desired metal ion, the alcohol in question acting as the solvent. The alcoholate can either be employed directly or prepared in situ from metal and alcohol.

In this case, I is usually isolated by concentrating the reaction solution or by adding an unpolar precipitant, eg. an aromatic such as benzene, toluene and the xylenes, a hydrocarbon such as n-pentane, n-hexane, petroleum ether and cyclohexane, or an ether such as diethyl ether, diisopropyl ether and methyl tert-butyl ether, and the crystalline or amorphous product of interest is separated off.

Moreover, other salts can be prepared from cyclohexenone oxime ether metal salts I where $R^b$=alkali metal ion by means of double decomposition. To this end, the aqueous solution of a salt I which is readily soluble in water, eg. the sodium salt, is usually treated with a (usually aqueous) solution of a metal halide or metal sulfate. If desired, the double decomposition reaction can be carried out in the presence of a solvent which is miscible with water, eg. a cyclic ether such as tetrahydrofuran and dioxane or a lower alcohol, or in the presence of a solvent which is not miscible with water, eg. an aromatic such as toluene and the xylenes, an ether such as diethyl ether, diisopropyl ether and methyl tert-butyl ether, a ketone such as acetone, a halogenated hydrocarbon such as methylene chloride and chloroform or a higher alcohol such as 2-ethylhexanol.

If the solubility in water of the desired salt I is suitably low, it starts to precipitate out of the reaction mixture.

If the solubility in an organic solvent which is not miscible with water is sufficiently high, the desired salt I can also be extracted using this solvent. Dissolved halide usually remains in the aqueous phase.

The cyclohexenone oxime ether metal salts I can be obtained from their preparation in the form of isomer mixtures which, however, can be separated, if desired, using the methods which are customary for this purpose, such as crystallization or chromatography, or else on an optically active adsorbate, to give the pure isomers. Pure optically active isomers can expediently be prepared from suitably optically active starting materials (II).

The cyclohexenone oxime ether metal salts I, both in the form of the isomer mixtures and in the form of the pure isomers, are suitable as herbicides. In general, they are tolerated, and thus selective, in broad-leaved crops and in monocotyledon plants (monocots) which do not belong to the Gramineae. Some of the salts I according to the invention are also suitable for the selective control of undesirable grasses in Gramineae crops. This effect is particularly pronounced at low application rates.

Depending on the application method in question, the compositions according to the invention can also be used in a number of other crop plants for eliminating undesirable plants. Suitable crops are, for example, the following:

*Allium cepa, Ananas comosus, Arachis hypogaea, Asparagus officinalis, Beta vulgaris* spec. *altissima, Beta vulgaris* spec. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Ficus elastica, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum,* Malus spec., *Manihot esculenta, Medicago sativa,* Musa spec., *Nicotiana tabacum* (*N. rustica*), *Olea europaea, Oryza sativa, Phaseolus lunatus, Phaseolus vulgaris, Picea abies,* Pinus spec., *Pisum sativum, Prunus avium, Prunus persica, Pyrus communis, Ribes sylestre, Ricinus communis, Saccharum officinarum, Secale cereale, Solanum tuberosum, Sorghum bicolor* (*S. vulgare*), *Theobroma cacao, Trifolium pratense, Triticum aestivum, Triticum durum, Vicia faba, Vitis vinifera, Zea mays.*

Moreover, the cyclohexenone oxime ether metal salts I can also be used in crops which are tolerant to the action of herbicides as a result of breeding, including genetic engineering methods.

The cyclohexenone oxime ether metal salts I, or the herbicidal compositions comprising them, can be applied, for example, in the form of directly sprayable aqueous solutions, powders, suspensions, also highly concentrated aqueous, oily or other suspensions or dispersions, emulsions, oil dispersions, pastes, dusts, materials for spreading or granules, by means of spraying, atomizing, dusting, spreading or pouring. The use forms depend entirely on the intended purposes; in any case, they should guarantee the finest possible distribution of the salts I according to the invention.

Suitable inert auxiliaries are essentially mineral oil fractions of medium to high boiling point, such as kerosine and diesel oil, furthermore coal tar oils and oils of vegetable or animal origin, aliphatic, cyclic and aromatic hydrocarbons, eg. paraffins, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, eg. amines such as N-methylpyrrolidone, and water.

Aqueous use forms can be prepared from emulsion concentrates, suspensions, pastes, wettable powders or water-dispersible granules by adding water. To prepare emulsions, pastes or oil dispersions, the substrates, either as such or dissolved in oil or solvent, can be homogenized in water by means of a wetting agent, tackifier, dispersant or emulsifier. Alternatively, it is possible to prepare concentrates comprising active ingredient, wetting agent, tackifier, dispersant or emulsifier and, if desired, solvent or oil, which are suitable for dilution with water.

Suitable surfactants are the alkali metal salts, alkaline earth metal salts and ammonium salts of aromatic sulfonic acids, eg. ligno-, phenol-, naphthalene- and dibutylnaphthalenesulfonic acid, or of fatty acids, alkyl- and alkylarylsulfonates, alkyl, lauryl ether and fatty alcohol sulfates, and salts of sulfated hexa-, hepta- and octadecanols and of fatty alcohol glycol ether, condensates of sulfonated naphthalene and its derivatives with formaldehyde, condensates of naphthalene, or of the naphthalenesulfonic acids, with phenol and formaldehyde, polyoxyethylene octylphenol ether, ethoxylated isooctyl-, octyl- or nonylphenol, alkylphenyl polyglycol ethers, tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors or methylcellulose.

Powders, materials for spreading and dusts can be prepared by mixing or grinding the active ingredients together with a solid carrier.

Granules, eg. coated granules, impregnated granules and homogeneous granules, can be prepared by binding the active ingredients to solid carriers. Solid carriers are mineral earths such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate, ammonium nitrate, ureas and products of vegetable origin such as cereal meal, tree bark meal, wood meal and nutshell meal, cellulose powders or other solid carriers.

The concentrations of the active ingredients I in the ready-to-use preparations can be varied within a wide range, for example from 0.001 to 98% by weight, preferably 0.01 to 95% by weight. The active ingredients are employed in a purity of from 90% to 100%, preferably 95% to 100% (according to NMR spectrum).

The salts I according to the invention or their preparation can be applied pre- or post-emergence, mainly by foliar application. If the active ingredients are less well tolerated by certain crop plants, application techniques can be used in which the herbicidal compositions are sprayed, with the aid of the spraying equipment, in such a way that they come into as little contact as possible, if any, with the leaves of the sensitive crop plants while the active ingredients reach the leaves of undesirable plants growing underneath, or the naked soil surface (post-directed, lay-by).

The application rates of active ingredient I are from 0.001 to 3.0, preferably 0.01 to 1.0, kg of active ingredient (a.i.)/ha, depending on the intended aim, the season, the target plants and the growth stage. Application can be effected by customary spraying techniques, for example using water as the carrier, in amounts of approximately 100 to 1000 l of spray mixture per ha.

The herbicidal compositions can be applied by the so-called "low-volume" or "ultra-low-volume" method, or in the form of granules.

To widen the spectrum of action and to achieve synergistic effects, the cyclohexenone oxime ether metal salts I may be mixed with a large number of representatives of other groups of herbicidal or growth-regulating active ingredients and then applied concomitantly. Suitable components for mixtures are for example 1,2,4-thiadiazoles, 1,3,4-thiadiazoles, amides, aminophosphoric acid and its derivatives, aminotriazoles, anilides, aryloxy-/hetaryloxyalkanoic acids and their derivatives, benzoic acid and its derivatives, benzothiadiazinones, 2-(hetaroyl/aroyl)-1,3-cyclohexanediones, hetaryl aryl ketones, benzylisoxazolidinones, meta-$CF_3$-phenyl derivatives, carbamates, quinolinecarboxylic acid and its derivatives, chloroacetanilides, cyclohexane-1,3-dione derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- and hetaryloxyphenoxypropionic esters, phenylacetic acid and its derivatives, 2-phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides and uracils.

The following are especially suitable:

N-(butoxymethyl)-2-chloro-N-(2,6-diethylphenyl)-acetamide (common name: butachlor), 2-(1,3-benzothiazol-2-yloxy)-N-methyl-acetanilide (common name: mefenacet), 3,7-Dichloroquinoline-8-carboxylic acid (common name: quinclorac), S-(4,6-dimethoxypyrimidin-2-ylcarbamoylsulfamoyl)-O-toluic [sic] acid methyl ester (common name: bensulfuron-methyl), 3-isopropyl-1H-2,1,3-benzothiadiazine-4-(3H)-one 2,2-dioxides [sic] (common name: bentazone), N-(ethylthio-carbonyl)-azepan (common name: molinate), S-4-chlorobenzyl N,N-diethylthiocarbamate (common name: thiobencarb), N-(2-propoxyethyl)-2-chloro-N-(2,6-diethylphenyl)acetamide (common name: pretilachlor), 3,5-bis(methylthio-carbonyl)-2-difluoromethyl-4-(2-methylpropyl)-6-trifluoromethylpyridine, (common name: dithiopyr), ethyl 2-[4-(6-chlorobenzoxazol-2-yloxy)phenoxy]propionate (common name: fenoxaprop ethyl), N-(2-phenylprop-2-ylthiocarbonyl) piperidine (common name: dimepiperate), 4-(2,4-dichlorobenzoyl)-1,3-dimethylpyrazol-5-yl toluene-4-sulfonate (common name: pyrazolynate, pyrazolate), 2-[4-(2,4-dichlorobenzoyl)-1,3-dimethyl-pyrazol-5-yloxy]acetophenone (common name: pyrazoxyfen), 2-[4-(2,4-dichloromtoluyl)-1,3-dimethylpyrazol-5- yloxy-4'-methylacetophenone (common name: benzofenap), 2-(2-naphthyloxy)propionanilide (common name: naproanilide), methyl 5-(4,6-dimethoxypyrimidin-2-ylcarbamoylsulfamoyl)-1-methylpyrazole-4-carboxylate (common name: pyrazosulfuron-ethyl), 1-(4,6-dimethoxy-1,3,5-triazin-2-yl)-3-[2-(2-methoxyethoxy)phenylsulfonyl]urea (common name: cinosulfuron), 2-bromo-3,3-dimethyl-N-(1-methyl-1-phenylethyl)butyramide (common name: bromobutide), 1-(1-methyl-1-phenylethyl)-3-p-toluylurea (common name: dymrone, daimuron), $N^2$-(1,2-dimethylpropyl)-$N^4$-ethyl-6-methylthio-1,3,5-triazin-2,4-diamine (common name: dimethametryne), S-benzyl 1,2-dimethylpropyl(ethyl)thiocarbamate (common name: esprocarb), (Z)-N-but-2-enyloxymethyl-2-chloro-2',6'-diethylacetanilide (common name: butenachlor), S-2-methylpiperidinocarbonylmethyl O,O-dipropyl phosphorodithioate (common name: piperophos), (1RS, 2SR,4SR)-1,4-epoxy-p-menth-2-yl 2-methylbenzylether (common name: cinmethylin), N-(3,4-dichlorophenyl)propanamide (common name: propanil), α-chloro-N-(3-methoxy-2-thienyl)methyl-2',6'-dimethylacetanilide, 4-ethoxybenz-2',3'-dihydrochloroanilide, 1-diethylcarbamoyl-3-(2,4,6-trimethylphenylsulfonyl)-1,2,4-triazole, 3-(2-chlorophenylmethyl)-1(1-methyl-1-phenylethyl)urea [sic], 2-(2-chloro-4-mesylbenzoyl)cyclohexane-1,3-dione, 2,4-dichlorophenoxyacetic acid (common name: 2,4-D), N-(2-chloroimidazole[1,2-a]pyridin-3-ylsulfonyl)-N'-(4,6-dimethoxy-2-pyrimidyl)urea (common name: Imazosulfuron), 1-{[2-(cyclopropylcarbonyl)phenyl]aminosulfonyl}-3-(4,6-dimethoxypyrimidin-2-yl)urea, 1-(4,6-dimethoxypyrimidin-2-yl)-3-[1-methyl-4-(2-methyl-2H-tetrazol-5-yl)pyrazol-5-ylsulfonyl]urea, 4-(4-chloro-2-methylphenoxy)butyric acid (common name: MCPB), 2,4-bis(ethylamino)-6-methylthio-1,3,5-triazines [sic] (common name: simetryn), [[(4,6-dimethoxy-2-pyrimidinyl)amino]carbonyl]-2-ethoxyphenyl ester (common name: ethoxysulfuron).

It may furthermore be useful to apply the cyclohexenone oxime ether metal salts I, alone or in combination with other herbicides, together with other crop protection agents, for example pesticides or agents for controlling phytopathogenic fungi or bacteria. Also of interest is the miscibility with mineral salt solutions which are used for treating nutritional and trace element deficiencies. Non-phytotoxic oils and oil concentrates can also be added.

PREPARATION EXAMPLES

Example 1

Preparation of 2-{1-[2-(4-chlorophenoxy)propyloximino]butyl}-5-tetrahydrothiopyran-3-ylcyclohexane-1,3-dione sodium salt A solution of sodium hydroxide (1.04 g) in 13.4 ml of water was added to a solution of 2-{1-[2-(4-chlorophenoxy)propyloximino]butyl}-5-tetrahydrothiopyran-3-ylcyclohexane-1,3-dione (12.4 g) in 10 ml of toluene, with vigorous stirring. After 20 minutes, the aqueous phase was separated off and concentrated in vacuo. Yield: 11.5 g of the desired sodium salt.

In a further experiment, the product of interest was freed from water by means of freeze-drying.

Example 2

Preparation of 2-{1-[2-(4-chlorophenoxy)propyloximino]butyl}-5-tetrahydrothiopyran-3-ylcyclohexane-1,3-dione potassium salt Example 1 was repeated using 1.81 g of potassium hydroxide in place of sodium hydroxide. Concentration of the aqueous phase in vacuo gave 12.0 g of the desired potassium salt.

Example 3

Preparation of 2-{1-[2-(4-chlorophenoxy)propyloximino]butyl}-5-tetrahydrothiopyran-3-ylcyclohexane-1,3-dione magnesium salt A solution of magnesium ethanolate (90 g) in 0.5 l of methanol was added dropwise at 20–30° C. to a solution of 2-{1-[2-(4-chlorophenoxy)propyloximino]butyl}-5-tetrahydrothiopyran-3-ylcyclohexane-1,3-dione (698 g) in 1.5 l of methanol. After the addition had ended, the reaction mixture was heated to reflux for 2 more hours. The methanol was then distilled off.

Residual methanol was displaced by adding toluene and then concentrating the mixture completely. For purification, the residue was stirred in methyl tert-butyl ether and then separated off again. Drying gave 556 g of the desired magnesium salt.

Example 4

Preparation of 2-{1-[2-(4-chlorophenoxy)propyloximino]butyl}-5-tetrahydrothiopyran-3-ylcyclohexane-1,3-dione calcium salt A suspension of calcium hydroxide (0.2 g) in 30 ml of methanol was added to a solution of 2-{1-[2-(4-chlorophenoxy)propyloximino]butyl}-5-tetrahydrothiopyran-3-ylcyclohexane-1,3-dione (2.5 g) in 80 ml of methanol with vigorous stirring. The mixture was subsequently stirred for 5 hours at room temperature, whereupon the solvent was removed in vacuo. Yield: 2.6 g of calcium salt.

Example 5

Preparation of 2-{1-[2-(4-chlorophenoxy)propyloximino]butyl}-5-tetrahydrothiopyran-3-ylcyclohexane-1,3-dione lithium salt A solution of 2-{1-[2-(4-chlorophenoxy)propyloximino]butyl}-5-tetrahydrothiopyran-3-ylcyclohexane-1,3-dione (300 g) in 900 ml of methyl tert-butyl ether was added with vigorous stirring to a solution of lithium hydroxide (16.8 g) in 500 ml of water. The resulting amount of solids was then separated off and dried in a vacuum drying oven. Yield: 285 g of the lithium salt, purity 97%.

Example 6

Preparation of 2-{1-[2-(4-chlorophenoxy)propyloximino]butyl}-5-tetrahydrothiopyran-3-ylcyclohexane-1,3-dione lithium salt A solution of lithium hydroxide (1.85 g) in 60 ml of water was added with vigorous stirring to a solution of 2-{1-[2-(4-chlorophenoxy)propyloximino]butyl}-5-tetrahydrothiopyran-3-ylcyclohexane-1,3-dione of (43.5 g) in 100 ml of toluene, whereupon the mixture was stirred overnight at room temperature. The resulting amount of solids was separated off and dried in a vacuum drying oven. Yield: 28 g of the lithium salt.

Example 7

Preparation of 2-{1-[2-(4-chlorophenoxy)propyloximino]butyl}-5-tetrahydrothiopyran-3-ylcyclohexane-1,3-dione lithium salt A solution of lithium hydroxide (1.85 g) in 60 ml of water was added with vigorous stirring to a solution of crude 2-{1-[2-(4-chlorophenoxy)propyloximino]butyl}-5-tetrahydrothiopyran-3-ylcyclohexane-1,3-dione crude product (56.7% pure; 43.5 g) in 100 ml of methyl tert-butyl ether. After the mixture had been stirred at room temperature for 2 hours, the resulting solid content was separated off and dried in a vacuum drying oven. 27.1 g of the lithium salt were obtained in a purity of 86.8% (yield: 94.3% of theory).

Example 8

Preparation of 2-{1-[2-(4-chlorophenoxy)propyloximino]butyl}-5-tetrahydrothiopyran-3-ylcyclohexane-1,3-dione sodium salt A solution of sodium hydroxide (2.64 g) in 90 ml of water was added to a solution of 2-{1-[2-(4-chlorophenoxy)propyloximino]butyl}-5-tetrahydrothiopyran-3-ylcyclohexane-1,3-dione (purity 90.5%; 32.4 g) in 100 ml of toluene. After the mixture had been stirred for ¼ hour at room temperature, the phases were separated. Yield: 142.4 g of an aqueous solution of the product of interest.

Example 9

Preparation of 2-{1-[2-(4-chlorophenoxy)propyloximino]butyl}-5-tetrahydrothiopyran-3-ylcyclohexane-1,3-dione lithium salt by sodium/lithium exchange Half of the sodium salt solution obtained in Example 8 was cooled to 10° C. and added dropwise to a cold solution (10° C.) of lithium chloride (1.4 g) in 110 ml of water. The mixture was stirred overnight at room temperature, whereupon the solids content was separated off and dried. 13.4 g of the lithium salt were obtained in a purity of 97.8% (yield: 88% of theory).

Example 10

Preparation of 2-{1-[2-(4-chlorophenoxy)propyloximino]butyl}-5-tetrahydrothiopyran-3-ylcyclohexane-1,3-dione lithium salt by sodium/lithium exchange The second half of the sodium salt solution obtained in Example 8 was cooled to 10° C. and added dropwise to a cold mixture (10° C.) of 100 ml of methyl tert-butyl ether and a solution of lithium chloride (1.4 g) in 110 ml of water. The mixture was subsequently stirred overnight at room temperature, whereupon the solids content was separated off and dried. 12.5 g of the lithium salt were obtained in a purity of 99.5% (yield: 84% of theory).

Tests for Physical Properties

1) Water Vapor Uptake (Hygroscopicity)

To determine the water vapor uptake, the test samples of active ingredient were first dried in vacuo for 48 hours at 50° C. and subsequently exposed to relative atmospheric humidities of 32%, 52% or 66% at an ambient temperature of 20° C. The weight increase of the active ingredient samples was then measured over a period of 14 days.

Table 2 shows the water vapor uptake of various salts of 2-{1-[2-(4-chlorophenoxy)propyloximino]butyl}-5-tetrahydrothiopyran-3-ylcyclohexane-1,3-dione (as a percentage with respect to the initial weight):

TABLE 2

| Salt | relative atmospheric humidity | | |
|---|---|---|---|
| | 32% | 52% | 66% |
| Lithium salt | 0% | 0.3% | 0.5% |
| Magnesium salt | 0% | 1% | 2% |
| Sodium salt | 3% | 8% | 11% |
| Potassium salt | 4% | 8% | 12% |

2) DSC[1] Plots
[1] Differential Scanning Calorimetry

The measurements were carried out in a temperature range of from 20 to 400° C. using a heating rate of 5 K/min. Prior to measurement, the active ingredient samples were dried. The measurements were carried out using a DSC 200 apparatus by Netzsch.

Figure 2:
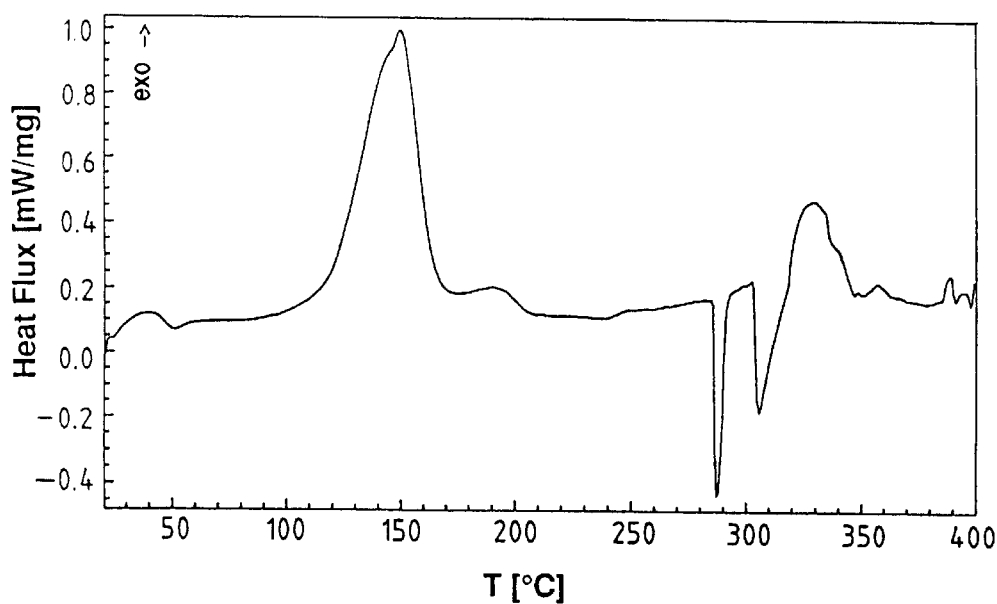
FIG. 2: DSC plot of the sodium salt of 2-{1-[2-(4-chlorophenoxy)propyloximino]butyl}-5-tetrahydrothiopyran-3-ylcyclohexane-1,3-dione.
Figure 3:
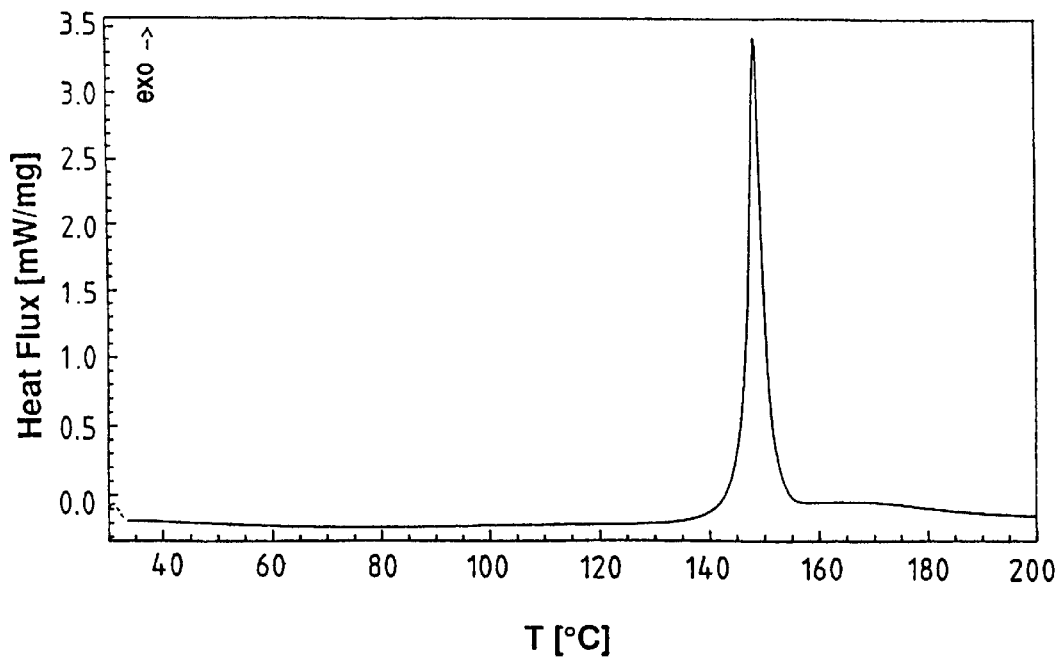
FIG. 3: DSC plot of the magnesium salt of 2-{1-[2-(4-chlorophenoxy)propyloximino]butyl}-5-tetrahydrothiopyran-3-ylcyclohexane-1,3-dione.
Figure 4:
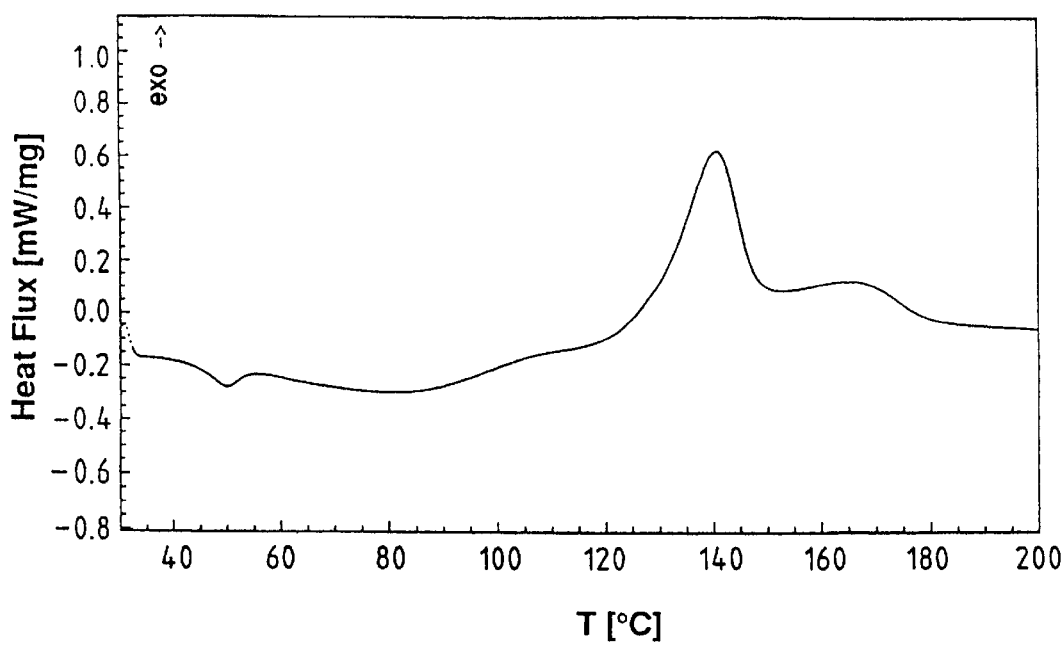
FIG. 4: DSC plot of the calcium salt of 2-{1-[2-(4-chylorophenoxy)propyloximino]butyl}-5-tetrahydrothiopyran-3-ylcyclohexane-1,3-dione.

The DSC plots of the lithium, sodium, magnesium and calcium salts of 2-{1-[2-(4-chlorophenoxy)propyloximino]butyl}-5-tetrahydrothiopyran-3-ylcyclohexane-1,3-dione [FIGS. 1 to 4] show that decomposition only takes place above approximately 140° C.

3) Shelf Life

To this end, the various active ingredient samples were stored for a certain time at various temperatures in tightly sealed glass containers. The active ingredient content of the samples was subsequently determined and compared with the comparison value at the beginning of storage (zero value). Table 3 shows the active ingredient content relative to the zero value.

Table 3

Comparison of the stability of various salts of 2-{1-[2-(4-chlorophenoxy)propyloximino]butyl}-5-tetrahydrothiopyran-3-ylcyclohexane-1,3-dione (II) after storage over 3 months:

| Salt | Shelf life at | | | |
|---|---|---|---|---|
| | 20° C. | 30° C. | 40° C. | 50° C. |
| Sodium salt | 100% | 87% | 43% | — |
| Magnesium salt | 100% | 98% | 93% | 81% |
| Lithium salt | 100% | 100% | 100% | 100% |

In the case of the free compound (II) {in the form of an 87% pure technical-grade active ingredient}, in contrast, the relative active ingredient content after 3 months' storage at 20° C. was only 69%.

FORMULATION EXAMPLES

Example 11

Emulsion Concentrate 10 parts by weight of 2-{1-[2-(4-chlorophenoxy)propyloximino]butyl}-5-tetrahydrothiopyran-3-ylcyclohexane-1,3-dione lithium salt were dissolved in a mixture composed of 80 parts by weight of an alkylated benzene and 20 parts by weight of the adduct of 8 mol of ethylene oxide to one mol of nonylphenyl [sic]. A stable emulsion concentrate was obtained.

| Example 12: | 5% granule formulation |
|---|---|
| 5% by weight of | 2-{1-[2-(4-chlorophenoxy)propyloximino]-butyl}-5-tetrahydrothiopyran-3-ylcyclohexane-1,3-dione magnesium salt, |
| 3% by weight of | phenolsulfonic acid/formaldehyde condensate, |
| 3% by weight of | phenol/formaldehy [sic]/sulfite condensate, |
| 20% by weight of | sodium metasilicate and |
| to 100% | chalk | were mixed intimately and ground using a high-speed rotor mill. The mixture was subsequently moistened with water and extruded using a basket extruder. The resulting granules were dried. After rapid storage for 14 days at 54° C., the active ingredient content was still 88% of the zero value.

Example 13:  Water-dispersible powder
12.5% by weight of 2-{1-[2-(4-chlorophenoxy)propyloximino]butyl}-5-tetrahydrothiopyran-3-ylcyclohexane-1,3-dione lithium salt,
7% by weight of naphthalenesulfonic acid/formaldehyde condensate,
14% by weight of sodium lignosulfonate,
3% by weight of phenolsulfonic acid/formaldehyde condensate and
to 100% chalk
were mixed intimately and ground using a high-speed rotor mill. A water-dispersible powder was obtained.

Example 14: water-dispersible granules
70% by weight of 2-{1-[2-(4-chlorophenoxy)propyloximino]-butyl}-5-tetrahydrothiopyran-3-ylcyclohexane-1,3-dione lithium salt and
to 100% by weight of naphthalenesulfonic acid/formaldehyde condensate were mixed intimately and then ground using a high-speed rotor mill, moistened and extruded using a granule extruder. The resulting granules were dried. After rapid storage at 54° C. for 14 days, the active ingredient content was still 99% of the initial value.

USE EXAMPLE

Herbicidal activity of the cyclohexenone oxime ether metal salts I was demonstrated by the following greenhouse experiments:

The culture containers used were plastic flowerpots containing loamy sand with approximately 3.0% of humus as the substrate. The seeds of the test plants were sown separately for each species.

In the case of the pre-emergence treatment, the active ingredients, which were suspended or emulsified in water, were applied directly after sowing by means of finely distributing nozzles. The containers were irrigated gently to promote germination and growth and subsequently covered with translucent plastic hoods until the plants had rooted. This cover results in uniform germination of the test plants, unless germination was adversely affected by the active ingredients.

For the post-emergence treatment, the test plants were first grown to a plant height of 3 to 15 cm, depending on the plant habit, and only then treated with the active ingredients, which were emulsified or suspended in water. The test plants were either sown directly and grown in the same containers or grown separately as seedlings and transplanted to the test containers a few days before the treatment. The application rate for the post-emergence treatment was 0.25 kg/ha of a.i. (active ingredient).

The plants were kept at 10–25° C. or 20–35° C., depending on the species. The test period extended over 2 to 4 weeks. During this time, the plants were tended, and their response to the individual treatments was evaluated.

Evaluation was carried out using a scale from 0 to 100. 100 means no emergence of the plants or complete destruction of at least the aerial parts, and 0 means no damage or normal course of growth.

The plants used in the greenhouse experiments belonged to the following species:

| Scientific Name | Common Name |
| --- | --- |
| Echinochloa crus-galli | barnyard grass |
| Leptochloa filiformis | red sprangletop |
| Setaria viridis | green foxtail |

At an application rate of 0.25 kg of a.i./ha, the 2-{1-[2-(4-chlorophenoxy)propyloximino]butyl}-5-tetrahydrothiopyran-3-ylcyclohexane-1,3-dione lithium salt was highly effective against the abovementioned grass weeds when applied post-emergence.

We claim:

1. A cyclohexenone oxime ether metal salt of the formula I

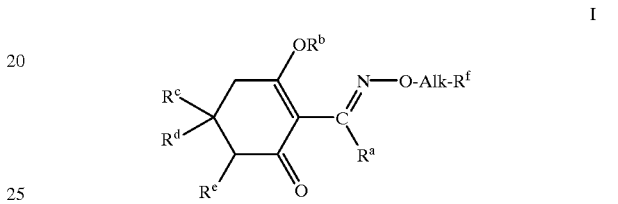

where the variables have the following meanings:
$R^a$ is $C_1$–$C_6$-alkyl;
$R^b$ is a lithium ion or one equivalent of a magnesium ion;
$R^c$ is hydrogen, cyano, formyl, $C_1$–$C_6$-alkyl, $C_1$–$C_4$-alkoxy-$C_1$–$C_6$-alkyl, $C_1$–$C_4$-alkylthio-$C_1$–$C_6$-alkyl, a phenoxy-$C_1$–$C_6$-alkyl, phenylthio-$C_1$–$C_6$-alkyl, pyridyloxy-$C_1$–$C_6$-alkyl or pyridylthio-$C_1$–$C_6$-alkyl group, it being possible for the phenyl and pyridyl rings of these groups to have attached to them, if desired, one to three substituents, in each case selected from the group consisting of nitro, cyano, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_3$–$C_6$-alkenyl, $C_3$–$C_6$-alkenyloxy, $C_3$–$C_6$-alkynyl, $C_3$–$C_6$-alkynyloxy and —$NR^gR^h$, where
$R^g$ is hydrogen, $C_1$–$C_4$-alkyl, $C_3$–$C_6$-alkenyl, $C_3$–$C_6$-alkynyl, $C_1$–$C_6$-acyl or benzoyl which, if desired, can have attached to it, in turn, a further one to three radicals, in each case selected from the group consisting of nitro, cyano, halogen, $C_1$–$C_4$-alkyl, $C_1$–$C_4$-haloalkyl, $C_1$–$C_4$-alkoxy and $C_1$–$C_4$-alkythio and
$R^h$ is hydrogen, $C_1$–$C_4$-alkyl, $C_3$–$C_6$-alkenyl or $C_3$–$C_6$-alkynyl;
a $C_3$–$C_7$-cycloalkyl group or a $C_5$–$C_7$-cycloalkenyl group, it being possible for these groups, if desired, to have attached to them one to three substituents, in each case selected from the group consisting of hydroxyl, halogen, $C_1$–$C_4$-alkyl, $C_1$–$C_4$-haloalkyl, $C_1$–$C_4$-alkoxy, $C_1$–$C_4$-alkylthio, benzylthio, $C_1$–$C_4$-alkylsulfonyl and $C_1$–$C_4$-alkylsulfinyl;
a 5-membered saturated heterocycle which, in addition to carbon atoms, contains one or two oxygen or sulfur atoms or one oxygen and one sulfur atom as ring members and which, if desired, can additionally have attached to it one to three substituents, in each case selected from the group consisting of $C_1$–$C_4$-alkyl, $C_1$–$C_4$-haloalkyl, $C_1$–$C_4$-alkoxy and $C_1$–$C_4$-alkylthio;
a 6- or 7-membered saturated or mono- or diunsaturated heterocycle which, in addition to carbon atoms, additionally contains one or two oxygen or sulfur atoms or one oxygen and one sulfur atom as ring members and which, if desired, can additionally have attached to it one to three substituents, in each case selected from the group consisting of hydroxyl, halogen, $C_1$–$C_4$-alkyl, $C_1$–$C_4$-haloalkyl, $C_1$–$C_4$-alkoxy and $C_1$–$C_4$-alkylthio;

a 5-membered heteroaromatic ring which, in addition to carbon atoms, contains one or two nitrogen atoms and one oxygen or sulfur atom, or one to three nitrogen atoms, or one oxygen or one sulfur atom as ring members and which, if desired, can additionally have attached to it one to three substituents, in each case selected from the group consisting of cyano, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_2$–$C_6$-alkenyl, $C_2$–$C_6$-alkenyloxy, $C_3$–$C_6$-alkynyloxy and $C_1$–$C_4$-alkoxy-$C_1$–$C_4$-alkyl;

phenyl- or pyridyl, both of which can, if desired, have attached to them one to three substituents, in each case selected from the group consisting of nitro, cyano, formyl, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_3$–$C_6$-alkenyl, $C_3$–$C_6$-alkenyloxy, $C_3$–$C_6$-alkynyl, $C_3$–$C_6$-alkynyloxy and —$NR^kR^l$, where $R^k$ is hydrogen, $C_1$–$C_4$-alkyl, $C_3$–$C_6$-alkenyl or $C_3$–$C_6$-alkynyl and $R^l$ is hydrogen, $C_1$–$C_4$-alkyl, $C_3$–$C_6$-alkenyl, $C_3$–$C_6$-alkynyl, $C_1$–$C_6$-acyl or benzoyl which, if desired, can additionally have attached to it, in turn, one to three substituents, in each case selected from the group consisting of nitro, cyano, halogen, $C_1$–$C_4$-alkyl, $C_1$–$C_4$-haloalkyl, $C_1$–$C_4$-alkoxy and $C_1$–$C_4$-alkylthio;

$R^d$ is hydrogen, hydroxyl or, if $R^c$ is $C_1$–$C_6$-alkyl, also $C_1$–$C_6$-alkyl;

$R^e$ is hydrogen, cyano, halogen, ($C_1$–$C_4$-alkoxy)carbonyl or ($C_1$–$C_4$-alkyl)ketoxime;

Alk is a $C_1$–$C_6$-alkylene chain, $C_3$–$C_6$-alkenylene chain or $C_3$–$C_6$-alkynylene chain, each of which can have attached to it a methylene group (=$CH_2$) and/or one to three substituents, in each case selected from the group consisting of halogen and $C_1$–$C_3$-alkyl;

a 3- to 6-membered alkylene or 4- to 6-membered alkenylene chain which, if desired, can have attached to it one to three $C_1$–$C_3$-alkyl substituents and which, in addition to methylene or methine units, contains one of the following bridge members: oxygen, sulfur, —SO—, —$SO_2$— or —N($R^i$)—, where $R^i$ is hydrogen, $C_1$–$C_4$-alkyl, $C_3$–$C_6$-alkenyl or $C_3$–$C_6$-alkynyl;

$R^f$ is the phenyl group, a halophenyl or a dihalophenyl group, it being possible for each phenyl ring, if desired, to have attached to it one to three substituents, in each case selected from the group consisting of nitro, cyano, formyl, halogen, $C_1$–$C_4$-alkyl, $C_1$–$C_4$-haloalkyl, $C_1$–$C_4$-alkoxy, $C_1$–$C_4$-haloalkoxy, $C_3$–$C_6$-alkenyl, $C_3$–$C_6$-alkenyloxy, $C_3$–$C_6$-alkynyl, $C_3$–$C_6$-alkynyloxy and —$NR^kR^l$, where $R^k$ is hydrogen, $C_1$–$C_4$-alkyl, $C_3$–$C_6$-alkenyl or $C_3$–$C_6$-alkynyl and $R^l$ is hydrogen, $C_1$–$C_4$-alkyl, $C_3$–$C_6$-alkenyl, $C_3$–$C_6$-alkynyl, $C_1$–$C_6$-acyl or benzoyl which, if desired, can additionally have attached to it, in turn, one to three radicals, in each case selected from the group consisting of nitro, cyano, halogen, $C_1$–$C_4$-alkyl, $C_1$–$C_4$-haloalkyl, $C_1$–$C_4$-alkoxy and $C_1$–$C_4$-alkylthio.

2. A herbicidal composition comprising a herbicidally active amount of at least one cyclohexenone oxime ether metal salt of the formula I as claimed in claim 1 and at least one inert liquid and/or solid carrier and, if desired, at least one surfactant.

3. A method of controlling undesirable vegetation, which comprises allowing a herbicidally active amount of at least one cyclohexenone oxime ether metal salt of the formula I as claimed in claim 1 to act on plants, their environment or on seed.

4. A process for the preparation of cyclohexenone oxime ether metal salts of the formula I as claimed in claim 1, which comprises reacting the corresponding free compounds II

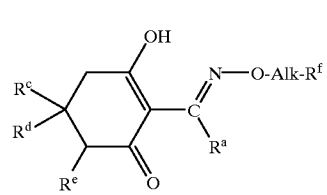

where $R^a$, $R^c$ to $R^f$ and alk have the same meanings as in formula I, with a metal hydroxide, metal hydride, metal ($C_1$–$C_5$-alkoxide) or metal carbonate.

5. The cyclohexenone oxime ether metal salt of claim 1, wherein $R^b$ is a lithium ion.

6. The cyclohexenone oxime ether metal salt of claim 1, wherein Alk is a 3- to 6-membered alkylene or 4- to 6-membered alkenylene chain which, if desired, can have attached to it one to three $C_1$–$C_3$-alkyl substituents and which, in addition to methylene or methine units, contains one of the following bridge members: oxygen, sulfur, —SO—, —$SO_2$— or —N($R^i$)—, where $R^i$ is hydrogen, $C_1$–$C_4$-alkyl, $C_3$–$C_6$-alkenyl or $C_3$–$C_6$-alkynyl.

7. The cyclohexenone oxime ether metal salt of claim 6, wherein $R^b$ is lithium.

8. The cyclohexanone oxime ether metal salt of claim 1, wherein $R^c$ is a 6- or 7-membered saturated or mono- or diunsaturated heterocycle which, in addition to carbon atoms, contains one or two oxygen or sulfur atoms or one oxygen and one sulfur atom as ring members, which is unsubstituted or substituted by one, two or three substituents selected from the group consisting of hydroxyl, halogen, $C_1$–$C_4$-haloalkyl, $C_1$–$C_4$-alkoxy and $C_1$–$C_4$-alkythio, and $R_d$ and $R_e$ are hydrogen.

9. The cyclohexenone oxime ether metal salt of claim 1, wherein $R^a$ is ethyl or n-propyl, $R^c$ is tetrahydropyran-3-yl, tetrahydropyran-4-yl or tetrahydrothiopyran-3-yl, $R^d$ and $R^e$ are hydrogen, and $R^f$ is halophenyl.

* * * * *

UNITED STATES PATENT AND TRADEMARK OFFICE
CERTIFICATE OF CORRECTION

PATENT NO. : 6,133,202  
DATED : October 17, 2000  
INVENTOR(S) : Bratz et al.

Page 1 of 1

It is certified that error appears in the above-identified patent and that said Letters Patent is hereby corrected as shown below:

Column 18, claim 8,
Line 51, after "halogen," insert --$C_1$-$C_4$-alkyl, --

Signed and Sealed this

Twenty-first Day of August, 2001

Attest:

*Attesting Officer*

NICHOLAS P. GODICI  
*Acting Director of the United States Patent and Trademark Office*